United States Patent [19]

Mills

[11] Patent Number: 5,214,201
[45] Date of Patent: May 25, 1993

[54] CRYSTALLIZATION OF OPTICAL ISOMERS OF LEUKOTRIENE ANTAGONISTS

[75] Inventor: Robert J. Mills, Norristown, Pa.

[73] Assignee: SmithKline Beecham Corporation, Philadelphia, Pa.

[21] Appl. No.: 806,031

[22] Filed: Dec. 12, 1991

[51] Int. Cl.$^5$ .................. C07B 57/00; C07D 403/14; C07D 307/36
[52] U.S. Cl. .................. 562/401; 548/253; 549/496; 560/12; 560/16; 562/426; 562/429; 562/430
[58] Field of Search .................. 562/401; 548/253; 560/12, 16; 549/496

[56] References Cited

U.S. PATENT DOCUMENTS

| | | | |
|---|---|---|---|
| 4,845,272 | 7/1989 | Nohira et al. | 562/401 |
| 4,904,822 | 2/1990 | Nohira et al. | 562/401 |
| 4,931,587 | 6/1990 | Piselli | 562/401 |
| 4,939,295 | 7/1990 | Merli et al. | 562/401 |

Primary Examiner—José G. Dees
Assistant Examiner—Vera C. Clarke
Attorney, Agent, or Firm—James M. Kanagy; Stuart R. Suter; Edward T. Lentz

[57] ABSTRACT

This invention relates to certain salts of leukotriene antagonists and the use of a particular amine to form these salts as a means for selectively crystallizing optical isomers of the leukotriene antagonists disclosed herein.

18 Claims, No Drawings

CRYSTALLIZATION OF OPTICAL ISOMERS OF LEUKOTRIENE ANTAGONISTS

SCOPE OF THE INVENTION

This invention relates to certain amine salts of leukotriene antagonists and the use of an amine to form these salts as a means for crystallizing selectively optical isomers of the leukotriene antagonists recited herein.

BACKGROUND OF THE INVENTION

"Slow Reacting Substance of Anaphylaxis" (SRS-A) has been shown to be a highly potent bronchoconstricting substance which is released primarily from mast cells and basophils on antigenic challenge. SRS-A has been proposed as a primary mediator in human asthma. SRS-A, in addition to its pronounced effects on lung tissue, also produces permeability changes in skin and may be involved in acute cutaneous allergic reactions. Further, SRS-A has been shown to effect depression of ventricular contraction and potentiation of the cardiovascular effects of histamine.

Antagonists to SRS substances have been developed in an attempt to provide relief from the disease conditions giving rise to or resulting from these compounds. A number of the compounds developed are normally prepared as a racemic mixture, though activity lies primarily or completely in just one of the optical isomers. Resolving these mixtures is a useful, if not necessary step, in preparing a useful formulation for treating these diseases. It has now been found that for certain compounds, the ones set out below, this can be accomplished most readily and inexpensively by means of (S)-α-methylbenzenemethanamine. This amine is uniquely suited to resolving certain enantiomers of the compounds given below so that the most active isomer can be obtained for use in treating SRS-related diseases.

DETAILED DESCRIPTION OF THE INVENTION

The compounds of this invention are (S)-α-methyl-benzenemethanamine salts of formula I

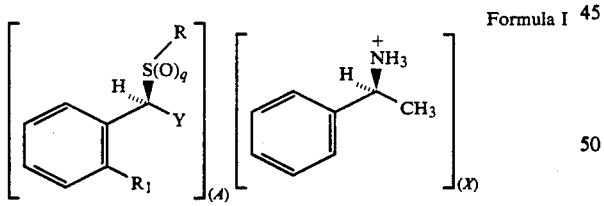

Formula I where:
A is 1 and X is 1 or 2;
$R_1$ is $C_8$ to $C_{13}$ alkyl, $C_7$ to $C_{12}$ alkoxy, $C_7$ to $C_{12}$ alkylthio, $C_{10}$ to $C_{12}$ 1-alkynyl, 10-undecynyloxy, 11-dodecynyl, phenyl-$C_4$ to $C_{10}$ alkyl, phenyl-$C_3$ to $C_9$ alkoxy, phenylthio-$C_3$ to $C_9$ alkyl with the phenyl optionally mono substituted with bromo, chloro, trifluoromethyl, $C_1$ to $C_4$ alkoxy, methylthio or trifluoromethylthio, furyl-$C_4$ to $C_{10}$ alkyl, trifluoromethyl-$C_7$ to $C_{12}$ alkyl or cyclohexyl-$C_4$ to $C_{10}$ alkyl;
q is 0, 1 or 2, with the proviso that $R_1$ is not alkylthio or phenylthioalkyl when q is 1 or 2;
Y is $(CH_2)_m COR_3$ or $(CH_2)_m$-tetrazol-5-yl;
$R_3$ is $O^-$, amino, or $C_1$ to $C_6$ alkoxy,
m is 0, 1, or 2;
R is $(CH_2)_n COR_6$;
n is 0 to 6;
$R_6$ is $O^-$, amino, or $C_1$ to $C_6$-alkoxy;
with the proviso that at least one of Y or R must have an $R_3$ or $R_6$ group respectively which is $O^-$.

This invention also relates to a process for separating an R or S isomer from a racemic mixture of a compound of formula II

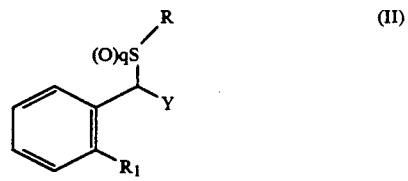

where R, $R_1$, q and Y are defined above with the proviso that $R_3$ and $R_6$ are $R_{3'}$ and $R_{6'}$ where $R_{3'}$ and $R_{6'}$ are independently —OH, amino, or $C_1$ to $C_6$ alkoxy, with the further proviso that at least one of $R_{3'}$ or $R_{6'}$ must be —OH or a salt thereof, which process comprises treating a racemic mixture of formula II with about 0.5 to 1.5 equivalents, relative to the number of carboxylic acid groups in the formula with (S)-α-methylbenzenemethanamine, recovering a crystalline salt, and converting the salt to an acid or a pharmaceutically acceptable salt. It is preferred to use 0.75 to 1.25 equivalents (1.1 is optimal) of the amine per carboxylic acid group in formula II. This process yields a substantially pure single enantiomer from a racemic mixture.

A preferred class of salts are those of formula (IA)

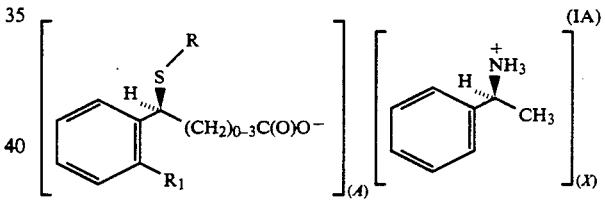

wherein A is 1, X is 1 or 2, and $R_1$ and R are described above.

A more preferred subgroup of these salts are 3-arylpropionates of formula (IB)

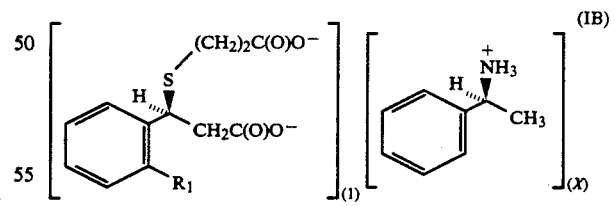

where $R_1$ is defined above, particularly where $R_1$ is phenylalkyl and X is 2. Most preferred among the salts of this group are:

the bis-(S)-α-methylbenzenemethanamine salt of (S)-β[(2-carboxyethyl)thio]-2-(1-dodecyl)benzenepropanoic acid; and the bis-(S)-α-methylbenzenemethanamine salt of (S)-β-[(2-carboxyethyl)thio]-2-(8-phenyloctyl)benzenepropanoic acid.

Another preferred group of salts are the aryl-acetates of formula (IC).

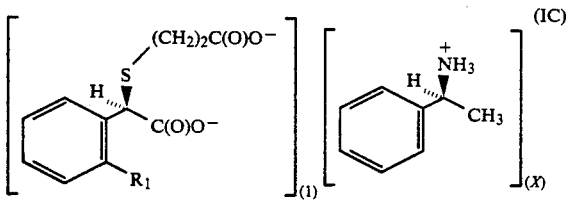

where $R_1$ is described above, particularly where $R_1$ is phenylalkyl and X is 2.

The salts of the formula (IC) are exemplified by the following compounds:

the bis-(S)-α-methylbenzenemethanamine salt of (R)-α-[(2-carboxyethyl)thio]-2-(1-dodecyl)benzeneacetic acid; and the bis-(S)-α-methylbenzenemethanamine salt of (R)-α-[(2-carboxyethyl)thio]-2-(8-phenyloctyl)benzeneacetic acid.

In a process for resolving racemates of formula II, the following sets of general and specific compounds are preferred.

A set of preferred racemates are those of formula (IIB),

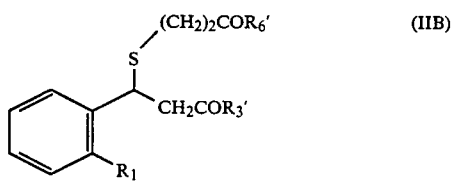

more particularly those where $R_1$ is a phenyl-$C_4$ to $C_{10}$-alkyl. Most particularly racemates of formula (IIB) can be treated with the (S)-α-methylbenzenemethanamine to obtain, after further manipulation, the isomers (S)-β-[(2-carboxyethyl)thio]-2-(1-dodecyl)benzenepropanoic acid and (S)-β-[(2-carboxyethyl)thio]-2-(8-phenyloctyl)benzenepropanoic acid.

Another set of preferred racemates are those of formula IIC

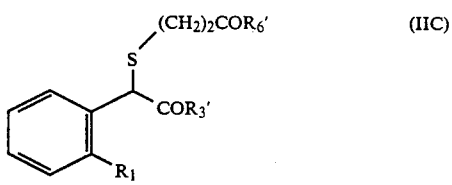

particularly those where $R_1$ is a phenyl-$C_4$ to $C_{10}$ alkyl. Most particularly racemates of formula (IIC) can be treated with (S)-α-methybenzenemethanamine to obtain, after further manipulation, the isomers (R)-α-[(2-carboxyethyl)thio]-2-(1-dodecyl)benzeneacetic acid and (R)-α-[(2-carboxyethyl)thio]-2-(8-phenyloctyl)benzeneacetic acid.

The racemates of this invention can be prepared according to the disclosure set out in U.S. Pat. No. 4,820,719 issued Apr. 11, 1989. That disclosure, in full, is incorporated herein by reference as if set out herein.

The amine, (S)-α-methylbenzenemethanamine, can be purchased as the free amine from a commercial source such as Schweizerhall, Inc.

This amine is a particularly effective resolving agent for separating out a particular isomer from a racemic mixture of compounds denoted by formula II. A salt is formed between the amine and the carboxylate function. This salt can be fractionally crystallized, giving a salt comprising the amine and just one isomer of the acid. 2-Propanol in acetonitrile is the preferred solvent system for crystallization. A mixture of 30% 2-propanol and 70% acetonitrile (volume/volume) is believed to be the optimal mixture. Isobutyl acetate, isopropyl acetate and ethyl acetate (undiluted) can also be used in place of the 2-propanol/acetonitrile mixture.

These salts may be converted to the corresponding acid by means of a dilute acid. Or they may be converted to another salt, such as an alkali metal salt, by treating a solution of the isolated salt with a base. For example, the salt can be converted to the free acid by treating a solution of that salt with dilute mineral acid, for example 0.5N HCl at room temperature or thereabouts. The mixture is then extracted with an appropriate organic solvent, or subjected to other convenient separatory means, and the pure isomer obtained as the free acid after removing the solvent.

The following examples illustrate the process for making and preparing the compounds of this invention. Being examples they are not to be considered as limiting the invention set forth in the claims appended hereto.

EXAMPLE 1

Preparation of (S)-β-[(2-Carboxyethyl)thio]-2-(8-phenyloctyl)benzenepropanoic acid using (S)-α-Methylbenzenemethanamine (1:2)

Racemic β-[(2-carboxyethyl)thio]-2-(8-phenyloctyl)-benzenepropionic acid 67.2 g (74.7%, 113.4 mmole) was dissolved in 203 mL of 2-propanol and 474 mL of acetonitrile and treated with 30.5 g (99%, 249 mmol) of (S)-α-methylbenzenemethanamine. Under an atmosphere of nitrogen, the mixture was heated to reflux over a period of 30 minutes, then allowed to cool to ambient temperature over a period of approximately 2.5 hours. When at 37° C., 0.5 g of seed crystals of authentic (S)-β-[(2-carboxyethyl)thio]-2-(8-phenyloctyl)benzenepropanoic acid, compound with (S)-α-methylbenzenemethanamine (1:2) were added. The mixture was stirred at ambient temperature for approximately 38 hours before cooling to 0°-5° C. After stirring at 0°-5° C. for 4 hours, the resulting solids were isolated by filtration. Chiral HPLC analysis indicated 97.8% of the desired S enantiomer. After recystallizing from 2-propanol (30%) in acetonitrile (70%), the content of the S-enantiomer was enhanced to >99.0%.

EXAMPLE 2

Determination and Confirmation of Absolute Configuration (S)-β-[(2-carboxyethyl)thio]-2-(8-phenyloctyl)benzenepropanoic acid reacts with two molar equivalents of (R)-4-iodo-α-methylbenzenemethanamine to produce a highly crystalline salt. For this salt, the absolute configuration of the diacid portion was determined unambiguously by single crystal x-ray analysis.

In order to correlate this information to the salt obtained in Example 1, the salt was treated with aqueous acid and extracted with ethyl acetate. By analyzing the extract on an HPLC column [cellulose Tris-(3,5-dimethylphenylcarbamate) chiral stationary phase, coated on silica gel] and comparing retention times to authentic samples of the racemates, it was determined that the diacid portion of the salt from Example 1 possessed the S-configuration.

I claim:

1. A salt of formula I

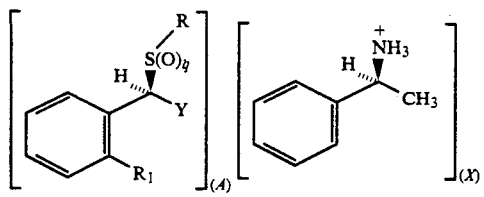

where:

A is 1 and X is 1 or 2;

$R_1$ is $C_8$ to $C_{13}$ alkyl, $C_7$ to $C_{12}$ alkoxy, $C_7$ to $C_{12}$ alkylthio, $C_{10}$ to $C_{10}$ 1-alkynyl, 10-undecynyloxy, 11-dodecynyl, phenyl-$C_4$ to $C_{10}$ alkyl, phenyl-$C_3$ to $C_9$ alkoxy, phenylthio-$C_3$ to $C_9$ alkyl wherein the phenyl may be mono substituted with bromo, chloro, trifluoromethyl, $C_1$ to $C_4$ alkoxy, methylthio or trifluoromethylthio, furyl-$C_4$ to $C_{10}$ alkyl, trifluoromethyl-$C_7$ to $C_{12}$ alkyl or cyclohexyl-$C_4$ to $C_{10}$ alkyl;

q is 0, 1 or 2, with the proviso that $R_1$ is not alkylthio or phenylthioalkyl when q is 1 or 2;

Y is $(CH_2)_m COR_3$, or $(CH_2)_m$-tetrazol-5-yl;

$R_3$ is $O^-$, amino, or $C_1$ to $C_6$ alkoxy;

m is 0, 1, or 2;

R is $(CH_2)_n COR_6$;

n is 0 to 6;

$R_6$ is $O^-$, amino, or $C_1$ to $C_6$-alkoxy;

with the proviso that at least one of Y or R must have an $R_3$ or $R_6$ group respectively which is $O^-$.

2. A salt of claim 1 represented by formula (IA).

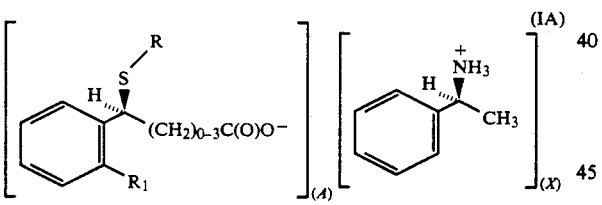

where $R_1$ is phenylalkyl.

3. A salt of claim 2 where R is $(CH_2)_{1-3} COR_6$.

4. A salt of claim 3 represented by the 3-arylpropionate of formula (IB) where X is 2

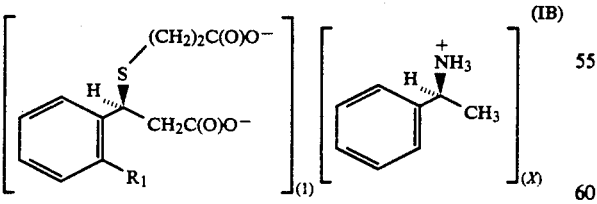

5. A salt of claim 4 where $R_1$ is phenyl-$C_4$ to $C_{10}$ alkyl.

6. A salt of claim 5 which is the bis-(S)-α-methylbenzenemethanamine salt of (S)-β-[(2-carboxyethyl)thio]-2-(1-dodecyl)benzenepropanoic acid.

7. A salt of claim 5 which is the bis-(S)-α-methylbenzenemethanamine salt of (S)-β-[(2-carboxyethyl)thio]-2-(8-phenyloctyl)benzenepropanoic acid.

8. A salt of claim 3 represented by formula (IC) where X is 2.

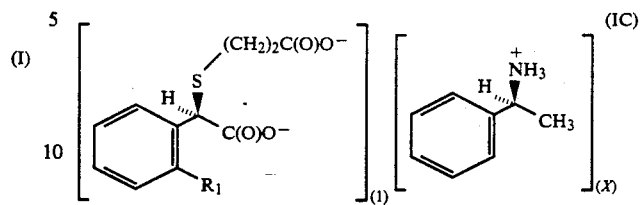

9. A salt of claim 8 where $R_1$ is a phenyl-$C_4$ to $C_{10}$ alkyl.

10. A salt of claim 9 which is the bis-(S)-α-methylbenezenemethanamine salt of (R)-α-[(2-carboxyethyl)-thio]-2-(1-dodecyl)benzeneacetic acid.

11. A salt of claim 9 which is the bis-(S)-α-methylbenezenemethanamine salt of (R)-α-[(2-carboxyethyl)-thio]-2-(8-phenyloctyl)benzeneacetic acid.

12. A process for separating a single isomer from a racemic mixture of a compound of formula II

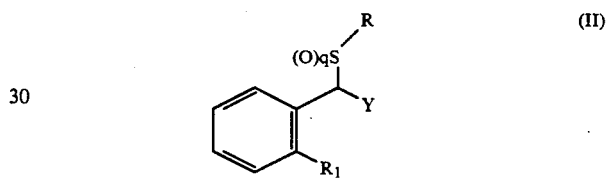

where:

$R_1$ is $C_8$ to $C_{13}$ alkyl, $C_7$ to $C_{12}$ alkoxy, $C_7$ to $C_{12}$ alkylthio, $C_{10}$ to $C_{12}$ 1-alkynyl, 10-undecynyloxy, 11-dodecynyl, phenyl-$C_4$ to $C_{10}$ alkyl, phenyl-$C_3$ to $C_9$ alkoxy, phenylthio-$C_3$ to $C_9$ alkyl wherein the phenyl may be mono substituted with bromo, chloro, trifluoromethyl, $C_1$ to $C_4$ alkoxy, methylthio or trifluoromethylthio, furyl-$C_4$ to $C_{10}$ alkyl, trifluoromethyl-$C_7$ to $C_{12}$ alkyl or cyclohexyl-$C_4$ to $C_{10}$ alkyl;

q is 0, 1 or 2, with the proviso that $R_1$ is not alkylthio or phenylthioalkyl when q is 1 or 2;

Y is $(CH_2)_m COR_{3'}$, or $(CH_2)_m$-tetrazol-5-yl;

$R_{3'}$ is OH, amino, or $C_1$ to $C_6$ alkoxy, m is 0, 1, or 2;

R is $(CH_2)_n COR_{6'}$;

n is 0 to 6;

$R_{6'}$ is OH, amino, or $C_1$ to $C_6$-alkoxy;

with the proviso that at least one of $R_{3'}$ or $R_{6'}$ is —OH or a salt thereof, which process comprises:

(i). treating a racemic mixture of formula II with between about 0.5 to 1.5 equivalents, relative to the number of carboxylic acid groups in formula (II), of (S)-α-methylbenzenemethanamine;

(ii). recovering a crystalline salt; and (iii). converting the salt to an acid or a pharmaceutically acceptable salt.

13. The process of claim 12 where the separated isomer is a compound of formula

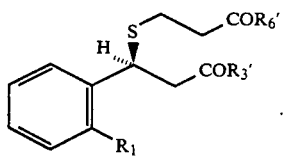

14. The process of claim 13 where $R_1$ is a phenyl-$C_4$ to $C_{10}$-alkyl.

15. The process of claim 14 which gives the isomer (S)-β-[(2-carboxyethyl)thio]-2-(1-dodecyl)benzenepropanoic acid, or (S)-β-[(2-carboxyethyl)thio]-2-(8-phenyloctyl)benzenepropanoic acid.

16. The method of claim 12 where the separated isomer is that of formula

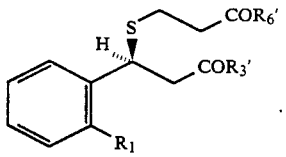

17. The process of claim 16 where $R_1$ is a phenyl-$C_4$ to $C_{10}$ alkyl.

18. The process of claim 17 which gives the isomer (R)-α-[(2-carboxyethyl)thio]-2-(1-dodecyl)benzeneacetic acid or (R)-α-[(2-carboxyethyl)thio]-2-(8-phenyloctyl)benzeneacetic acid.

* * * * *